United States Patent [19]

Ternansky

[11] Patent Number: 5,084,447

[45] Date of Patent: Jan. 28, 1992

[54] C-3 PHOSPHINE OXIDE SUBSTITUTED CARBACEPHALOSPORINS

[75] Inventor: Robert J. Ternansky, Indianapolis, Ind.

[73] Assignee: Eli Lilly and Company, Indianapolis, Ind.

[21] Appl. No.: 691,254

[22] Filed: Apr. 25, 1991

[51] Int. Cl.$^5$ .................. C07D 463/00; C07F 9/576; A61K 31/675

[52] U.S. Cl. ...................... 514/80; 540/205

[58] Field of Search .................. 540/205; 514/80

[56] References Cited

U.S. PATENT DOCUMENTS 4,291,031 9/1981 Takaya et al. .................. 424/246

OTHER PUBLICATIONS

Nishide et al., *Chem. Pharm. Bull.* 36(7) 2354–2361 (1988), "A Synthesis of New 3-Dialkoxyphosphinylmethyl and 3-Dihydroxyphosphinylmethyl Cephalosporins".

Ziegler and Schwartz, *J. Org. Chem.*, vol. 43, No. 5, 985–991 (1978), "Synthetic Studies on Lignan Lactones: Aryl Dithiane Route to (±)-Podorhizol[1] and (±)-Isopodophyllotoxone and Approaches to the Stegane Skeleton".

Corbel et al., *Synthesis 1048–1051, (1985),* "An Efficient Synthesis of Dialkyl 2-Oxoalkanephonates and Diphenyl-2-Oxoalkylphosphine Oxides from 1-Chloralkyl Ketones".

Bhattacharya and Thyagarajan, *Chem. Rev.*, vol. 81, No. 4, 415–430 (1981), "The Michaelis-Arbuzov Rearrangement".

Tavs and Weitkamp, *Tetrahedron,* vol. 26, 5529–5534, (1970), "Herstellung Und KMR-Spektren Einiger α,-β-Ungesattigter Phosphonsaureester Nickelsalzkatalysierte Reaktion Von Vinylhalogeniden Mit Trialkylphosphiten".

*Primary Examiner*—Mark L. Berch
*Attorney, Agent, or Firm*—James J. Sales; Leroy Whitaker

[57] ABSTRACT

This invention provides novel 3-phosphine oxide substituted 1-carba(1-dethia)cephalosporins useful as antimicrobial agents, and formulations and methods of use thereof.

14 Claims, No Drawings

C-3 PHOSPHINE OXIDE SUBSTITUTED CARBACEPHALOSPORINS

BACKGROUND OF THE INVENTION

This invention relates to 1-carba(1-dethia)cephalosporin antibiotics, intermediates for the preparation thereof, to pharmaceutical formulations comprising the antibiotics, and to a method for the treatment of infectious diseases in man and animals.

The preparation of 1-carbacephalosporins and C-3 substituted methyl derivatives thereof is taught broadly by Christensen et al., in U.S. Pat. No. 4,226,866. Hirata et al., in U.K. patent application No. 2041923, teach a method for preparing 3-H and 3-halo 1-carbacephalosporins, while Hatanaka et al., *Tetrahedron Letters*, 24, 4837–4838 (1983), teach a method for preparing a 3-hydroxy-($\pm$)-1-carbacephalosporin. A variety of 3-hydroxy-1-carbacephalosporins are also provided in EPO Patent Application Publication 209,352 while their 3-triflate (3-trifluoromethanesulfonic acid) esters are disclosed in EPO Patent Application Publication 211,540.

Takaya in U.K. patent application No. 2043644A discloses 3-phosphonocephalosporanic acid derivatives. Nishide et al. in *Chem. Pharm. Bull.*, 36, 2354–2361 (1988), teaches the synthesis of 3-dialkoxyphosphinylmethyl and 3-dihydroxyphosphinylmethyl cephalosporins.

Although many safe and potent antibiotics of the $\beta$-lactam class are known and used clinically, the research into this class of compounds continues in an effort to find antibiotics with improved efficacy, particularly against microorganisms insensitive or resistant to the known antibiotics.

SUMMARY OF THE INVENTION

This invention provides novel C-3 phosphine oxide substituted carbacephalosporins. More specifically, this invention provides compounds of the Formula (I)

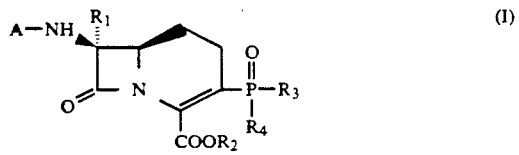

wherein $R_1$ is hydrogen, $C_1$–$C_4$ alkoxy, $C_1$–$C_4$ alkylthio, or the formido group —NHCHO; $R_2$ is hydrogen, a biologically labile group, or a carboxy-protecting group; $R_3$ and $R_4$ independently are —$OR_{11}$ or —$R_{11}$ wherein $R_{11}$ is $C_1$–$C_6$ alkyl, $C_2$–$C_6$ alkenyl, $C_2$–$C_6$ alkynyl, $C_1$–$C_6$ substituted alkyl, $C_2$–$C_6$ substituted alkenyl, $C_2$–$C_6$ substituted alkynyl, phenyl, or a substituted phenyl group represented by the formula

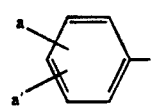

wherein a and a' independently are hydrogen, halogen, hydroxy, $C_1$–$C_4$ alkoxy, $C_1$–$C_4$ alkanoyloxy, $C_1$–$C_4$ alkyl, $C_1$–$C_4$ alkylthio, amino, $C_1$–$C_4$ alkanoylamino, $C_1$–$C_4$ alkylsulfonylamino, carboxy, carbamoyl, hydroxymethyl, aminomethyl, or carboxymethyl;

and A is hydrogen, an amino-protecting group, or an acyl group of the formula

wherein R is the residue of a carboxylic acid; and the pharmaceutically acceptable salts thereof.

DETAILED DESCRIPTION OF THE INVENTION

"Phosphine oxide" is defined to be a pentavalent phosphorus double bonded to an oxygen. The term phosphinylidene is defined to be synonymous to phosphine oxide.

The term "residue of a carboxylic acid" includes those 7-position side chains known in the cephalosporin and carbacephalosporin arts, and those 6-position side chains known in the penicillin art, wherein R of the formula RC(O)— may be a $C_1$–$C_{20}$ residue of a carboxylic acid, which includes $C_1$–$C_6$ alkyl, $C_1$–$C_6$ alkyl substituted by cyano, carboxy, halogen, amino, $C_1$–$C_4$ alkoxy, $C_1$–$C_4$ alkylthio, trifluoromethyl, trifluoromethylthio, naphthyl, a phenyl or a substituted phenyl group represented by the formula

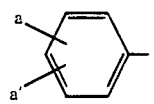

wherein a and a' are as defined previously;
a group represented by the formula

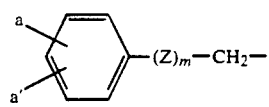

wherein a and a' are defined as above, Z is O or S, and m is 0 or 1;

a heteroarylmethyl group represented by the formula

wherein $R_5$ is thienyl, furyl, benzothienyl, benzofuryl, indolyl, triazolyl, tetrazolyl, oxazolyl, thiazolyl, oxadiazolyl, thiadiazolyl, and such heteroaryl groups substituted by amino, hydroxy, halogen, $C_1$–$C_4$ alkyl, $C_1$–$C_4$ alkoxy, or $C_1$–$C_4$ alkylsulfonylamino;

a substituted methyl group represented by the formula

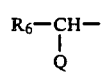

wherein $R_6$ is cyclohex-1,4-dienyl, or an optionally substituted phenyl group represented by the formula

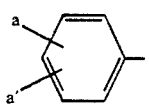

wherein a and a' have the above defined meanings, or $R_6$ is $R_5$ as defined above, and Q is amino, hydroxy, $C_1$–$C_4$ alkanoyloxy, carboxy, sulfoamino, or a substituted amino group of the formula

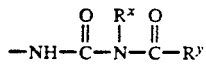

wherein $R^x$ is hydrogen or $C_1$–$C_3$ alkyl, $R^y$ is $C_1$–$C_4$ alkyl, furyl, thienyl, phenyl, halophenyl, nitrophenyl, styryl, halostyryl, nitrostyryl or a group of the formula

wherein $R^x$ has the same meanings as defined above and $R^z$ is hydrogen, $C_1$–$C_3$ alkylsulfonyl, $C_1$–$C_3$ alkyl, or $C_1$–$C_4$ alkanoyl; or Q is a substituted amino group of the formula

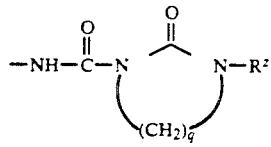

wherein $R^z$ has the same meanings as defined above, and q is 2 or 3; or Q is a substituted amino group of the formula

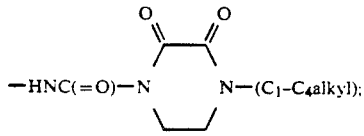

or Q is a benzamido group of the formula

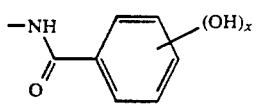

wherein X is 1 to 3; or Q is a pyridonylcarbonylamino group of the formula

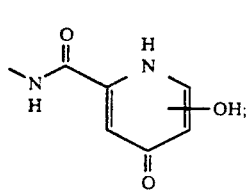

or Q is a pyridylcarbonylamino group of the formula

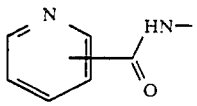

said group optionally substituted by $C_1$–$C_4$ alkyl, amino, carboxy, hydroxy or halogen; or Q is an imidazolyl or pyrazolyl group of the formula

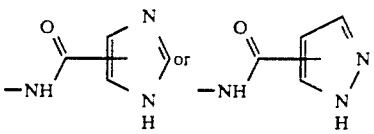

and said imidazolyl or pyrazolyl optionally substituted by $C_1$–$C_4$ alkyl, carboxy, amino, or halogen; or Q is a benzpyridazin-4-one group represented by the formula

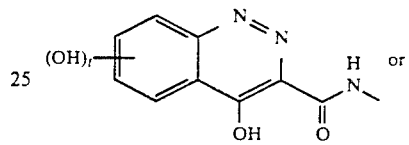

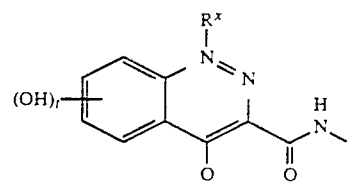

wherein $R^x$ is hydrogen or $C_1$–$C_3$ alkyl, and t is 1 to 3; or Q is a benzpyranone group of the formula

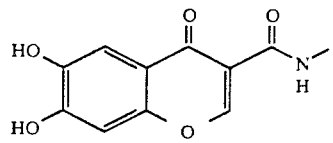

or R is a group represented by the formula

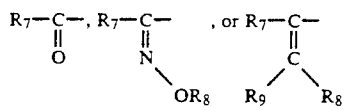

wherein $R_7$ is $R_5$ or $R_6$ as defined above, $R_9$ is hydrogen or halogen, and $R_8$ is hydrogen, $C_1$–$C_4$ alkyl, or a carboxy-substituted alkyl or cycloalkyl group represented by the formula

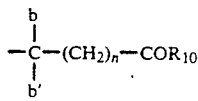

wherein b and b' independently are hydrogen or $C_1$–$C_3$ alkyl, or b and b', when taken together with the carbon to which they are bonded, form a 3- to 6-membered carbocyclic ring, n is 0–3, and $R_{10}$ is hydroxy, $C_1$–$C_4$ alkoxy, amino, $C_1$–$C_4$ alkylamino, or di($C_1$-$C_4$ alkyl)amino; or $R_8$ is $C_1$-$C_4$ substituted by phenyl or phenyl substituted by one or two of the same or different groups selected from among $C_1$-$C_4$ alkyl, hydroxy, halogen, carboxy or protected carboxy; or $R_8$ is $C_1$-$C_4$ alkyl substituted by amino or protected amino; or $R_8$ is $C_2$-$C_4$ alkenyl; or $R_8$ is a cyclic lactam group of the formula

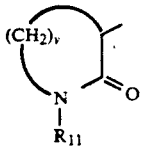

wherein v is 2-4 and $R_{11}$ is hydrogen or $C_1$-$C_3$ alkyl; or $R_8$ is a heteroaryl methyl group of the formula

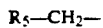

wherein $R_5$ has the same meanings as defined hereinabove.

The compounds represented by the formula I wherein A is an acyl group, RCO, wherein R is the residue of a $C_1$-$C_{20}$ carboxylic acid as herein above described, and $R_2$ is hydrogen or a biologically labile group, and the pharmaceutically acceptable salts thereof, inhibit the growth of microorganisms pathogenic to man and animals. The compounds which are protected (A=an amino protecting group and/or $R_4$=carboxy-protecting group), or deprotected (A=hydrogen), are useful as intermediates as described hereinafter.

In the above definition of the compounds represented by the Formula I, "$C_1$-$C_6$ alkyl" refers to the straight and branched chain alkyl groups such as methyl, ethyl, n-propyl, isopropyl, n-butyl, s-butyl, t-butyl, n-pentyl, n-hexyl, 3-methylpentyl, and like alkyl groups; $C_1$-$C_6$ substituted includes those $C_1$-$C_6$ alkyls substituted with cyano, carboxy, halogen, amine, $C_1$-$C_4$ alkoxy, $C_1$-$C_4$ alkylthio, trifluoromethyl, and trifluoromethylthio, "$C_1$-$C_6$ alkyl substituted by cyano" refers to cyanomethyl, cyanoethyl, 4-cyanobutyl, and the like; "$C_1$-$C_6$ alkyl substituted by ... carboxy" refers to such groups as carboxymethyl, 2-carboxyethyl, 2-carboxypropyl, 4-carboxybutyl, 5-carboxypentyl, and the like; "$C_1$-$C_6$ alkyl substituted by ... halogen" refers to chloromethyl, bromomethyl, 2-chloroethyl, 1-bromoethyl, 4-chlorobutyl, 4-bromopentyl, 6-chlorohexyl, 4-fluorobutyl, 3-fluoropropyl, fluoromethyl, and the like; "$C_1$-$C_6$ alkyl substituted by ... amino" refers to such groups as 2-aminoethyl, aminomethyl, 3-aminopropyl and 4-aminobutyl; "$C_1$-$C_6$ alkyl substituted by ... $C_1$-$C_4$ alkoxy" refers to methoxy-methyl, 2-methoxyethyl, 2-ethoxyethyl, ethoxymethyl, 3-propoxypropyl, 3-ethoxybutyl, 4-t-butoxybutyl, 3-methoxypentyl, 6-methoxyhexyl, and like groups; "$C_1$-$C_6$ alkyl substituted by ... $C_1$-$C_4$-alkylthio" refers to such groups as for example methylthiomethyl, 2-methylthioethyl, 2-ethylthiopropyl, 4-methylthiobutyl, 5-ethylthiohexyl, 3-t-butylthiopropyl, and like groups; "$C_1$-$C_6$ alkyl substituted by ... trifluoromethyl" is exemplified by 2,2,2-trifluoroethyl, 3,3,3-trifluoropropyl, 4,4,4-trifluorobutyl, 6,6,6-trifluorohexyl, and the like; and "$C_1$-$C_6$ alkyl substituted by ... trifluoromethylthio" refers to, for example, trifluoromethylthiomethyl, 2-trifluoromethylthioethyl, 2-trifluoromethylthiopropyl, 4-trifluoromethylthiobutyl, 5-trifluoromethylthiohexyl, and like $C_1$-$C_6$ alkyl substituted groups.

The term "$C_2$-$C_6$ alkenyl" denotes groups possessing between two and six carbon atoms and at least one double carbon-carbon bond. A few examples of such groups are vinyl, 1-propene-2-yl, 1-butene-4-yl, 1-pentyne-5-yl, 1-butyne-1-yl, and like groups.

The term "$C_2$-$C_6$ substituted alkenyl" denotes groups possessing between two and six carbon atoms, at least one double carbon-carbon bond, and substituted with one or more of halo, carboxy, amino, $C_1$-$C_4$ alkoxy, $C_1$-$C_4$ alkylthio, trifluoromethyl, trifluoromethylthio, cyano, and the like.

The term "$C_2$-$C_6$ alkynyl" denotes those groups possessing between two and six carbon atoms and at least one triple carbon-carbon bond.

The term "$C_2$-$C_6$ substituted alkynyl" denotes the above $C_2$-$C_6$ alkynyl groups that are substituted by one or more halogen, hydroxy, protected hydroxy, amino, protected amino, $C_1$-$C_7$ acyloxy, nitro, carboxy, protected carboxy, carbamoyl, carbamoyloxy, cyano, methylsulfonylamino, or $C_1$-$C_4$ alkoxy groups. The $C_2$-$C_6$ substituted alkynyl groups may be substituted at least once with the same or different substituents.

The term "$C_1$-$C_4$ alkylthio" refers to those groups possessing one to four carbon atoms and substituted with at least one sulfur atom.

The terms "halo" and "halogen" refer to the fluoro, chloro, bromo or iodo groups.

In the Formula I, substituted phenyl groups wherein the substituent(s) are represented by a and a' are exemplified by such groups as halophenyl such as 4-chlorophenyl, 3-bromophenyl, 2-fluorophenyl, 2-iodophenyl, 2,4-dichlorophenyl, and 3,5-dichlorophenyl; hydroxyphenyl such as 2-hydroxyphenyl, 3-hydroxyphenyl, 4-hydroxyphenyl, 2,4-dihydroxyphenyl, and 3,4-dihydroxyphenyl; alkoxyphenyl, such as 2,6-dimethoxyphenyl, 4-methoxyphenyl, 3-ethoxyphenyl, 3,4-dimethoxyphenyl, 4-t-butoxyphenyl, 4-methoxy-3-ethoxyphenyl, and 4-n-propoxyphenyl; alkanoyloxyphenyl such as 2-acetoxyphenyl, 4-propionoxyphenyl, 4-formyloxyphenyl, 4-acetoxyphenyl, 3-butyryloxyphenyl, and 3-acetoxyphenyl; alkylphenyl such as 4-methylphenyl, 2-methylphenyl, 2,4-dimethylphenyl, 3-t-butylphenyl, 4-ethylphenyl, 4-ethyl-3-methylphenyl, and 3,5-dimethylphenyl; alkylthiophenyl such as 4-methylthiophenyl, 3-n-butylthiophenyl, 2-ethylthiophenyl, 3,4-dimethylthiophenyl, and 3-n-propylthiophenyl; aminophenyl such as 2-aminophenyl, 4-aminophenyl, 3,5-diaminophenyl, and 3-aminophenyl; alkanoylaminophenyl such as 2-acetylaminophenyl, 4-acetylaminophenyl, 3-propionylaminophenyl, and 4-butyrylaminophenyl; alkylsulfonylaminophenyl such as 3-methylsulfonylaminophenyl, 4-methylsulfonylaminophenyl, 3,5-di(methylsulfonylamino)phenyl, 4-n-butylsulfonylaminophenyl, and 3-ethylsulfonylaminophenyl; carboxyphenyl such as 2-, 3-, or 4-carboxyphenyl, 3,4-dicarboxyphenyl, and 2,4-dicarboxyphenyl; carbamoylphenyl such as 2-carbamoylphenyl, 2,4-dicarbamoylphenyl, and 4-carbamoylphenyl; hydroxymethylphenyl such as 4-hydroxymethylphenyl and 2-hydroxymethylphenyl; aminomethylphenyl such as 2-aminomethylphenyl and 3-aminomethylphenyl; and carboxymethylphenyl such as 2-carboxymethylphenyl, 4-carboxymethylphenyl, and 3,4-di(carboxymethyl)phenyl; and the substituted phenyl groups bearing different substituents such as 4-chloro-3-methylphenyl, 4-fluoro-3-hydroxyphenyl, 3,5-dichloro-4-hydroxyphenyl, 4-hydroxy-3-chlorophenyl, 4-hydroxy-3-methylphenyl, 4-ethyl-3-hydroxyphenyl, 4-methoxy-3-hydroxyphenyl, 4-t-butyloxy-2-hydroxyphenyl, 4-acetylamino-3-methoxyphenyl, 3-amino-4-ethylphenyl, 2-aminomethyl-4-chlorophenyl, 2-hydroxymethyl-3-methoxyphenyl, 2-hydroxymethyl-4-fluorophenyl, 2-acetoxy-4-aminophenyl, 4-acetoxy-3-methoxyphenyl, 3-isopropylthio-4-chlorophenyl, 2-methylthio-4-hydroxymethylphenyl, 4-carboxy-3-hydroxyphenyl, 4-ethoxy-3-hydroxyphenyl, 4-methylsulfonylamino-2-carboxyphenyl, 4-amino-3-chlorophenyl, and 2-carboxymethyl-4-hydroxyphenyl.

Examples of RCO— groups of the Formula I wherein R is a group represented by the formula

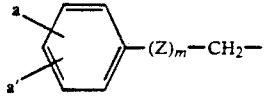

with m=0 are: phenylacetyl, 4-hydroxyphenylacetyl, 4-chlorophenylacetyl, 3,4-dichlorophenylacetyl, 4-methoxyphenylacetyl, 3-ethoxyphenylacetyl, 2-aminomethylphenylacetyl, 3-carboxyphenylacetyl, 4-acetoxyphenylacetyl, 3-aminophenylacetyl, and 4-acetylaminophenylacetyl; and with m=1 and Z=O, phenoxyacetyl, 4-chlorophenoxyacetyl, 4-fluorophenoxyacetyl, 3-aminophenoxyacetyl, 3-hydroxyphenoxyacetyl, 2-methoxyphenoxyacetyl, 2-methylthiophenoxyacetyl, 4-acetylaminophenoxyacetyl, 3,4-dimethylphenoxyacetyl, and 3-hydroxymethylphenoxyacetyl; and with m=1 and Z=S, phenylthioacetyl, 4-chlorophenylthioacetyl, 3,4-dichlorophenylthioacetyl, 2-fluorophenylthioacetyl, 3-hydroxyphenylthioacetyl, and 4-ethoxyphenylthioacetyl.

Examples of $R_5$—$CH_2CO$— groups of the Formula I wherein R is a heteroaryl group are: 2-thienylacetyl, 3-thienylacetyl, 2-furylacetyl, 2-benzothienylacetyl, 2-benzofurylacetyl, indol-2-ylacetyl, 1H-tetrazol-1-ylacetyl, oxazol-2-ylacetyl, oxazol-4-ylacetyl, thiazol-4-ylacetyl, 2-aminothiazol-4-ylacetyl, 1,3,4-oxadiazol-2-ylacetyl, 1,3,4-thiadiazol-2-ylacetyl, 5-ethyl-1,3,4-thiadiazol-2-ylacetyl, and like heteroaryl groups substituted by amino, $C_1$-$C_4$ alkylsulfonylamino, hydroxy, halo, $C_1$-$C_4$ alkyl or $C_1$-$C_4$ alkoxy groups.

Examples of RCO— groups of the Formula I compounds wherein R is a substituted methyl group represented by the formula $R_6$—CH(Q)— and Q is amino, carboxy, hydroxy, or sulfo, are 2-carboxy-2-phenylacetyl, 2-amino-2-(2-naphthalenyl)acetyl, 2-carboxy-2-(4-hydroxyphenyl)acetyl, 2-amino-2-phenylacetyl, 2-amino-2-(4-hydroxyphenyl)acetyl, 2-amino-2-(3-chloro-4-hydroxyphenyl)acetyl, 2-amino-2-(cyclohex-1,4-dien-1-yl)acetyl, 2-amino-2-(3-methylsulfonamidophenyl)acetyl, 2-amino-2-(3-ethylsulfonaminophenyl)acetyl, 2-hydroxy-2-phenylacetyl, 2-formyloxy-2-phenylacetyl, 2-sulfo-2-phenylacetyl, 2-sulfo-2-(4-methylphenyl)acetyl, and 2-acetoxy-2-(3-hydroxyphenyl)acetyl, 2-amino-2-(2-thienyl)acetyl, 2-amino-2-(3-benzothienyl)acetyl, 2-amino-2-(1H-tetrazol-1-yl)acetyl, 2-hydroxy-2-(1,3,4-thiadiazol-2-yl)acetyl, 2-amino-2-(2-aminothiazol-4-yl)acetyl, 2-carboxy-2-(2-thienyl)acetyl, 2-carboxy-2-(benzothien-2-yl)acetyl, and 2-hydroxy-2-(benzofur-2-yl)acetyl; and when Q is a substituted amino group represented by the formula

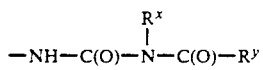

examples of such acyl groups are 2-(N-methyl-N-benzoylcarbamoylamino)-2-phenylacetyl, 2-(N-methyl-N-cinnamoylcarbamoylamino)-2-(2-furyl)acetyl, 2-(N,N-dimethylcarbamoylureido)-2-(4-chlorophenyl)acetyl, 2-[N-methyl-N-(2-chlorocinnamoyl)carboylamino]-2-(2-thienyl)acetyl, and 2-(N-ethyl-N-acetylcarbamoylamino)-2-(4-hydroxyphenyl)acetyl; and when Q is a substituted amino group represented by the formula

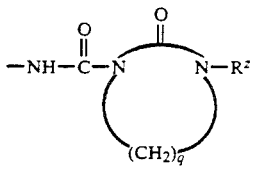

examples are 2-[(3-methylimidazolidin-2-one-1-yl)carbonylamino]-2-phenylacetyl, 2-[(3-acetylimidazolidin-2-one-1-yl)carbonylamino]-2-phenylacetyl, 2-[(3-methylsulfonylimidazolidin-2-one-1-yl)-2-(2-thienyl)acetyl, and 2-[(3-acetylhexahydropyrimidin-2-one-1-yl)carbonylamino]-2-phenylacetyl; and when Q is a hydroxy-substituted benzamido group represented by the formula

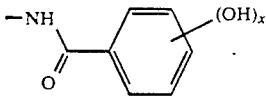

examples of such acyl groups are 2-(2,4-dihydroxybenzamido)-2-phenylacetyl, 2-(4-hydroxybenzamido)-2-(4-hydroxyphenyl)acetyl, 2-(3,4-dihydroxybenzamido)-2-(2-aminothiazol-4-yl)acetyl, 2-(3,5-dihydroxybenzamido)-2-(3-thienyl)acetyl, and 2-(2-hydroxybenzamido)-2-(2-benzofuryl)acetyl.

When Q is an hydroxy-substituted pyridinecarbonylamino group, examples include e.g., 2-hydroxypyridin-4-one-6-ylcarbonylamino and 3-hydroxypyridin-4-one-6-ylcarbonylamino. When Q is a pyridylcarbonylamino group examples are e.g., pyridin-3-ylcarbonylamino, 4-aminopyridin-3-ylcarbonylamino, 5-chloropyridin-2-ylcarbonylamino, 3-carboxypyridin-4-ylcarbonylamino, and 4-aminopyridino-2-ylcarbonylamino. When Q is an imidazole or pyrazole group as defined above examples include e.g., 2-aminoimidazol-4-ylcarbonylamino, 5-carboxy-2-methylimidazol-4-ylcarbonylamino, 5-carboxypyrazol-3-ylcarbonylamino, 3-aminopyrazol-4-ylcarbonylamino and 4-hydroxypyrazol-5-ylcarbonylamino. When Q is a benzpyridazin-4-one-3-ylcarbonylamino group, examples of Q are represented by the formulae

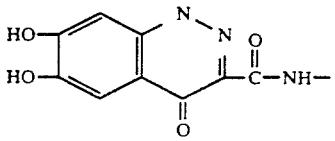

and

-continued

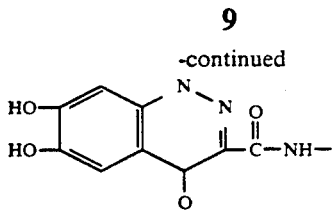

Examples of RCO acyl groups of the compounds represented by Formula I when R is a keto group or an oximino-substituted group represented by the formulae

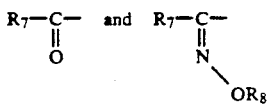

are the keto groups 2-oxo-2-phenylacetyl, 2-oxo-2-(2-thienyl)acetyl, 2-oxo-2-(2-aminothiazol-4-yl)acetyl; and oximino-substituted groups 2-phenyl-2-methoxyaminoacetyl, 2-(2-thienyl)-2-ethoxyiminoacetyl, 2-(2-furyl)-2-methoxyiminoacetyl, 2-(2-benzothienyl)-2-carboxymethoxyiminoacetyl, 2-(2-thienyl)-2-(2-carboxyethoxy)iminoacetyl, 2-(2-amino-1,2,4-thiadiazol-4-yl)-2-methoxyiminoacetyl, 2-(2-aminothiazol-4-yl)-2-methoxy-iminoacetyl, 2-(2-chlorothiazol-4-yl)-2-methoxyiminoacetyl, 2-(2-aminothiazol-4-yl)-2-(2-carboxyprop-2-yl)oxyiminoacetyl, 2-(2-aminothiazol-4-yl)-2-(2-carbamoylprop-2-yl)oxyiminoacetyl, and 2-(5-amino-1,3,4-thiadiazol-2-yl)-2-methoxyiminoacetyl.

When $R_8$ of formula (1) is $C_1-C_4$ alkyl substituted by phenyl or substituted phenyl, such groups are exemplified by benzyl, 4-hydroxybenzyl, 4-chlorobenzyl, 3-carboxybenzyl, 3-chloro-4-hydroxybenzyl, 2-phenylethyl, 1-phenylethyl, 3-phenylpropyl, 4-hydroxy-2-phenylpropyl, 3-phenylbutyl and like phenylalkyl groups.

When $R_8$ represents $C_1-C_4$ alkyl substituted by amino or protected amino, examples include 2-aminoethyl, 3-aminopropyl, 4-aminobutyl, 2-aminopropyl and such groups wherein the amino group is protected by an amino-protecting group.

When $R_8$ is a $C_2-C_4$ alkenyl group, examples include allyl, butene-2, butene-3, butene-1, and like groups.

Examples of the compounds represented by formula (1) when R is a group of the formula

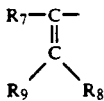

may be found in Hamashima, U.S. Pat. No. 4,634,617 incorporated herein by reference. Exemplary substituents are, for $R_9$, hydrogen, for $R_7$, phenyl, furyl, thienyl, oxazolyl, isoxazolyl, optimally protected aminoisoxazolyl, thiazolyl, optionally protected aminothiazolyl, thiadiazolyl, and aminothiazolyl, and for $R_6$, $C_1-C_3$ alkenyl and $-CH_2COO_2H$.

The term "organic or inorganic cation" refers to counter-ions for the carboxylate anion of a carboxylate salt. The counter-ions are chosen from the alkali and alkaline earth metals, such as lithium, sodium, potassium, barium and calcium; ammonium; and organic cations such as dibenzylammonium, benzylammonium, 2-hydroxyethylammonium, bis(2-hydroxyethyl)ammonium, phenylethylbenzylammonium, dibenzylethylenediammonium, and like cations. Other cations encompassed by the above term include the protonated forms of procaine, quinine and N-methylglucosamine, and the protonated forms of basic amino acids such as glycine, ornithine, histidine, phenylglycine, lysine and arginine. A preferred cation for the carboxylate anion is the sodium cation.

The term "carboxy-protecting group" as used in this document refers to conventional groups commonly used in the β-lactam art to block or protect the carboxylic acid group while reactions are carried out on other functional groups on the compound. Examples of such carboxylic acid protecting groups include benzyl, 4-nitrobenzyl, 4-methoxybenzyl, 3,4-dimethoxybenzyl, 2,4-dimethoxybenzyl, 2,4,6-trimethoxybenzyl, 2,4,6-trimethylbenzyl, pentamethylbenzyl, 3,4-methylenedioxybenzyl, benzhydryl, 4,4'-dimethoxybenzhydryl, 2,2',4,4'-tetramethoxybenzhydryl, t-butyl, t-amyl, trityl, 4-methoxytrityl, 4,4'-dimethoxytrityl, 4,4',4''-trimethoxytrityl, 2-phenylprop-2-yl, trimethylsilyl, t-butyldimethylsilyl, phenacyl, 2,2,2-trichloroethyl, 2-(trimethylsilyl)ethyl, 2-(di(n-butyl)methylsilyl)ethyl, 2-(p-toluenesulfonyl)ethyl, 2-(4-nitrobenzylsulfonyl)ethyl, allyl, cinnamyl, 1-(trimethylsilylmethyl)prop-1-en-3-yl, and like moieties. The species of carboxy-protecting group employed is not critical so long as the derivatized carboxylic acid is stable to the conditions of subsequent reaction(s) on other positions of the molecule and can be removed at the appropriate point without disrupting the remainder of the molecule. In particular, it is important not to subject the carboxy-protected 1-carbacephalosporin molecule to strong nucleophilic bases. Such harsh removal conditions are also to be avoided when removing amino-protecting groups and hydroxy-protecting groups, discussed below. Preferred carboxylic acid protecting groups are the benzhydryl, allyl and p-nitrobenzyl groups. Carboxy-protecting groups similar to those used in the cephalosporin, penicillin and peptide arts can also be used to protect a carboxy group substituents of the compounds provided herein. Further examples of these groups are found in E. Haslam, "Protective Groups in Organic Chemistry", J. G. W. McOmie, Ed., Plenum Press, New York, N.Y., 1973, Chapter 5, and T. W. Greene, "Protective Groups in Organic Synthesis", John Wiley and Sons, New York, N.Y., 1981, Chapter 5.

The term "amino-protecting group" as used in the specification refers to substituents of the amino group commonly employed to block or protect the amino functionality while reacting other functional groups on the compound. Examples of such amino-protecting groups include the formyl group, the trityl group, the phthalimido group, the trichloroacetyl group, the chloroacetyl, bromoacetyl and iodoacetyl groups, urethane-type blocking groups such as benzyloxycarbonyl, 4-phenylbenzyloxycarbonyl, 2-methylbenzyloxycarbonyl, 4-methoxybenzyloxycarbonyl, 4-fluorobenzyloxycarbonyl, 4-chlorobenzyloxycarbonyl, 3-chlorobenzyloxycarbonyl, 2-chlorobenzyloxycarbonyl, 2,4-dichlorobenzyloxycarbonyl, 4-bromobenzyloxycarbonyl, 3-bromobenzyloxycarbonyl, 4-nitrobenzyloxycarbonyl, 4-cyanobenzyloxycarbonyl, 1,1-diphenyleth-1-yloxycarbonyl, 1,1-diphenylprop-1-yloxycarbonyl, 2-phenylprop-2-yloxycarbonyl, 2-(p-toluyl)prop-2-yloxycarbonyl, cyclopentanyloxycarbonyl, 1-methylcyclopentanyloxycarbonyl, cyclohexanyloxycarbonyl, 1-methylcyclohexanyloxycarbonyl, 2-methylcyclohexanyloxycarbonyl, 2-(4-toluylsulfonyl)ethoxycarbonyl, 2-(methylsulfonyl)ethoxycarbonyl, 2-(triphenylphosphino)ethoxycarbonyl, 9-fluorenylmethoxycarbonyl ("FMOC"), 2-(trimethylsilyl)ethoxycarbonyl, allyloxycarbonyl, 1-(trimethylsilylmethyl)prop-1-en-3-yloxycarbonyl, 4-acetoxybenzyloxycarbonyl, 2,2,2-trichloroethoxycarbonyl, 2-ethynyl-2-propoxycarbonyl, cyclopropylmethoxycarbonyl, 4-(decyloxy)benzyloxycarbonyl, 1-piperidyloxycarbonyl and the like; the benzoylmethylsulfonyl group, the 2-(nitro)phenylsulfonyl group, the diphenylphosphine oxide group and like amino-protecting groups. The species of amino-protecting group employed is not critical so long as the derivatized amino group is stable to the condition of subsequent reaction(s) on other positions of the molecule and can be removed at the appropriate point without disrupting the remainder of the molecule. Preferred amino-protecting groups are the 1,2-bis(dimethylsilyl)ethylene (See, e.g., U.S. Pat. No. 4,558,124), benzyloxycarbonyl, p-nitrobenzyloxycarbonyl, allyloxycarbonyl, t-butoxycarbonyl, and trityl groups. Similar amino-protecting groups used in the cephalosporin, penicillin and peptide art are also embraced by the above terms. Further examples of groups referred to by the above terms are described by J. W. Barton, "Protective Groups In Organic Chemistry", J. G. W. McOmie, Ed., Plenum Press, New York, N.Y., 1973, Chapter 2, and T. W. Greene, "Protective Groups in Organic Synthesis", John Wiley and Sons, New York, N.Y., 1981, Chapter 7.

The term "pharmaceutically acceptable salt" refers to salts of the carboxy group or other acidic moiety in the molecule, such as a carboxy or sulfo substituent group, and includes salts formed with organic amines and inorganic bases. Such amines and bases include those whose counter-ions are chosen from the alkali and alkaline earth metals (such as lithium, sodium, potassium, barium and calcium); ammonium; and the organic cations (such as dibenzylammonium, benzyl ammonium, 2-hydroxyethylammonium, bis(2-hydroxyethyl)ammonium, phenylethylbenzylammonium, dibenzylethylenediammonium, and like cations). A preferred cation for the carboxylate anion is the sodium cation.

Furthermore, the term includes salts that form by standard acid-base reactions with basic groups of the compounds of this invention (such as amino groups) and organic or inorganic acids. Such acids include hydrochloric, sulfuric, phosphoric, acetic, succinic, citric, lactic, maleic, fumaric, palmitic, cholic, mucic, D-glutamic, d-camphoric, glutaric, phthalic, tartaric, lauric, stearic, salicyclic, methanesulfonic, benzenesulfonic, sorbic, picric, benzoic, cinnamic, and like acids.

The C-3 phosphine oxide substituted carbacephalosporins provided herein can be esterified with a biologically labile group to form esters which form the free acid antibiotic form in vivo. Biologically labile groups are acyloxymethyl groups represented by the formula

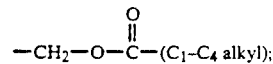

acyloxyalkyl groups represented by the formula

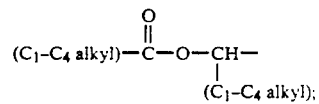

dialkyl ether groups represented by the formula $(C_1-C_4 alk)—O—CH_2CH_2—O—CH_2—$;

phthalidyl, indanyl, or the 5-methyl-2-oxo-1,3-dioxolen-4-methyl-4'-ylcyclocarbonate group represented by the formula

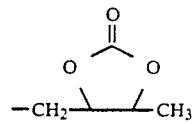

Examples of acyloxymethyl groups, $R_2$, are acetoxymethyl, propionoxymethyl and pivaloyloxymethyl. Acyloxyalkyl groups are exemplified by 1-acetoxyethyl, 1-acetoxypropyl, and 1-propionoxybutyl. Examples of dialkyl ether groups are β-methoxyethoxymethyl, β-ethoxyethoxymethyl, and β-t-butyloxyethoxymethyl.

The biologically labile esters of the C-3 phosphine oxide carbacephalosporins can be used as prodrugs and can provide ease of formulation and administration of the antibiotic.

Examples of the above defined C-3 phosphine oxide substituted carbacephalosporins are described below in Table 1 wherein the terms in the column headings refer to Formula (I).

TABLE 1

| A | $R_1$ | $R_2$ | $R_3$ | $R_4$ |
|---|---|---|---|---|
| acetyl | Hydrogen | H | Methoxy | Methoxy |
| n-propionyl | Methoxy | H | Ethoxy | Ethoxy |
| t-butyryl | Ethoxy | H | Propoxy | Propoxy |
| n-valeryl | Propoxy | H | Butoxy | Butoxy |
| 3-methylvaleryl | Butoxy | H | Isopropoxy | Isoporpoxy |
| cyanoacetyl | Methylthio | H | Isobutoxy | Isobutoxy |
| 4-cyanobutyryl | Ethylthio | H | Sec-Butoxy | Sec-Butoxy |
| 2-carboxyacetyl | Isopropylthio | H | Tert-Butoxy | Tert-Butoxy |
| 4-carboxybutyryl | n-Butylthio | H | Pentyloxy | Pentyloxy |
| chloroacetyl | Isobutylthio | H | Hexyloxy | Hexyloxy |
| bromoacetyl | Formamido | H | Isopentyloxy | Isopentyloxy |
| 4-fluorobutyryl | Hydrogen | H | Neopentyloxy | Neopentyloxy |
| 6-chlorohexanoyl | Methoxy | H | 3-Methylpentyloxy | 3-Methylpentyloxy |
| 2-aminoacetyl | Ethoxy | H | 3-Methylbutoxy | 3-Methylbutoxy |
| 4-aminobutyryl | Propoxy | H | 2-Ethylpropoxy | 3-Ethylpropoxy |
| methoxyacetyl | Butoxy | H | 2,2-Dimethylbutoxy | 2,2-Dimethylbutoxy |
| 6-methoxyhexanoyl | Ethylthio | H | Methoxy | Ethoxy |
| methylthioacetyl | Isopropylthio | H | Ethoxy | Propoxy |
| 2-ethylthio- | | | | |

TABLE 1-continued

| A | R₁ | R₂ | R₃ | R₄ |
|---|---|---|---|---|
| 2-amino-2-(3-propionyl | H | Pr-opoxy | Butoxy | |
| 3-t-butylthio-propionyl | isobutylthio | H | Butoxy | Isopropoxy |
| 4,4,4-trifluoro-butyryl | Hydrogen | H | Isobutoxy | Sec-Butoxy |
| trifluoromethyl-thioacetyl | Methoxy | H | Sec-Butoxy | Tert-Butoxy |
| 4-trifluoromethyl-thiobutyryl | Ethoxy | H | Tert-Butoxy | Pentyloxy |
| 4-chlorophenylacetyl | Propoxy | H | Pentyloxy | Hexyloxy |
| 3-bromophenyl-acetyl | Butoxy | H | Hexyloxy | Isopentyloxy |
| 2,4-dichloro-phenylacetyl | Methylthio | H | Isopentyloxy | Neopentyloxy |
| 2-hydroxyphenyl-acetyl | Ethylthio | H | Neopentyloxy | 3-Methylpentyloxy |
| 4-hydroxyphenyl-acetyl | Isopropylthio | H | 3-Methylpentyloxy | 3-Methylbutoxy |
| 2,6,-dimethoxy-phenylacetyl | Isobutylthio | H | 2-Ethylpropoxy | 2,2-Dimethyl-butoxy |
| 4-methoxy-3-ethoxyphenylacetyl | n-Butylthio | H | 2,2-Dimethyl-butoxy | 2,3-Dimethyl-butoxy |
| 2-acetoxyphenyl-acetyl | Isobutylthio | H | 2,3-Dimethyl-butoxy | Methoxy |
| 4-formyloxy-phenylacetyl | Formamido | H | Methyl | Methoxy |
| 3-butyryloxy-phenylacetyl | Hydrogen | H | Ethyl | Ethoxy |
| 3-t-butylphenyl-acetyl | Ethoxy | H | Butyl | Butoxy |
| 4-ethyl-3-methyl-phenylacetyl | Propoxy | H | Isopropyl | Isopropoxy |
| 4-methylthio-phenylacetyl | Butoxy | H | Isobutyl | Isobutoxy |
| 3-n-butylthio-phenylacetyl | Methiothio | H | Sec-Butyl | Sec-Butoxy |
| 3,4-dimethylthio-phenylacetyl | Ethylthio | H | Tert-Butyl | Tert-Butoxy |
| 2-aminophenyl-acetyl | Isopropylthio | H | Pentyl | Pentyloxy |
| 2-acetylamino-phenylacetyl | Isobutylthio | H | Isopentyl | Isopentyloxy |
| 3-propionylamino-phenylacetyl | Formamido | H | Neopentyl | Neopentyloxy |
| 3-methylsuflonyl-aminophenylacetyl | Hydrogen | H | 3-Methylpentyl | 3-Methylpentyloxy |
| 3,5-di(methyl-sulfonylamino)-phenylacetyl | Methoxy | H | 3-Methylbutyl | 3-Methylbutoxy |
| 3,4-dicarboxy-phenylacetyl | Ethoxy | H | 2-Ethylpropyl | 2-Ethylpropoxy |
| 4-carboxyphenyl-acetyl | Propoxy | H | 2,2-Dimethylbutyl | 2,2-Dimethyl-butoxy |
| 2,4-dicarbamoyl-phenylacetyl | Methylthio | H | Methoxy | Propoxy |
| 4-hydroxymethyl-phenylacetyl | Ethylthio | H | Ethoxy | Butoxy |
| 2-aminomethyl-phenylacetyl | Isopropylthio | H | Propoxy | Isopropoxy |
| 2-carboxymethyl-phenylacetyl | n-Butylthio | H | Butoxy | Isobutoxy |
| 4-chloro-3-methylphenylacetyl | Formamido | H | Isobutoxy | Tert-Butoxy |
| 4-hydroxy-3-chlorophenylacetyl | Hydrogen | H | Sec-Butoxy | Pentyloxy |
| 3-ethyl-4-hydroxyphenyl-acetyl | Methoxy | H | Tert-Butoxy | Hexyloxy |
| 4-t-butyloxy-2-hydroxyphenyl-acetyl | Ethoxy | H | Pentyloxy | Isopentyloxy |
| 3-amino-2-ethyl-phenylacetyl | Propoxy | H | Hexyloxy | Neopentyloxy |
| 2-hydroxymethyl-4-fluorophenyl-acetyl | Butoxy | H | Isopentyloxy | 3-Methylpentyloxy |
| 2-acetoxy-4-aminophenylacetyl | Methylthio | H | Neopentyloxy | 3-Methylbutoxy |

TABLE 1-continued

| A | R$_1$ | R$_2$ | R$_3$ | R$_4$ |
|---|---|---|---|---|
| 3-isopropylthio-4-chlorophenylacetyl | Ethylthio | H | 3-Methylpentyloxy | 2-Ethylpropoxy |
| 3-hydroxyphenyl-acetyl | n-Butylthio | H | 2-Ethylpropoxy | 2,3-Dimethyl-butoxy |
| 3,4-dichloro-phenylacetyl | Isobutylthio | H | 2,2-Dimethyl-butoxy | Methoxy |
| 4-methoxyphenyl-acetyl | Formamido | H | 2,3-Dimethyl-butoxy | Ethoxy |
| 3-aminomethyl-phenylacetyl | Hydrogen | H | Methoxy | Methoxy |
| 4-acetoxyphenyl-acetyl | Methoxy | H | Ethoxy | Ethoxy |
| 4-acetylamino-phenylacetyl | Ethoxy | H | Propoxy | Propoxy |
| phenoxyacetyl | Propoxy | H | Butoxy | Butoxy |
| 4-fluorophenoxy acetyl | Butoxy | H | Isopropoxy | Isopropoxy |
| 3-aminophenoxy-acetyl | Methylthio | H | Isobutoxy | Isobutoxy |
| 2-methylthio-phenoxyacetyl | Ethylthio | H | Sec-Butoxy | Sec-Butoxy |
| phenylthioacetyl | Isopropylthio | H | Tert-Butoxy | Tert-Butoxy |
| 2-fluorophenyl-thioacetyl | n-Butylthio | H | Pentyloxy | Pentyloxy |
| 2-furylacetyl | Formamido | H | Isopentyloxy | Isopentyloxy |
| 2-benzothienylacetyl | Hydrogen | H | Neopentyloxy | Neopentyloxy |
| indol-2-ylacetyl | Methoxy | H | 3-Methylpentyloxy | 3-Methylpentyloxy |
| thiazol-4-ylacetyl | Butoxy | H | 2,2-Dimethyl-butoxy | 2,2-Dimethyl-butoxy |
| 5-ethyl-1,3,4-thiadiazol-2-ylacetyl | Methylthio | H | 2,3-Dimethyl-butoxy | 2,3-Dimethyl-butoxy |
| 2-carboxy-2-phenylacetyl | Ethylthio | H | Methoxy | Methoxy |
| 2-amino-2-(4-hydroxyphenyl)-acetyl | Isopropylthio | H | Ethoxy | Ethoxy |
| 2-amino-2-(3-ethylsulfonyl-aminophenyl)acetyl | n-Butylthio | H | Propoxy | Propoxy |
| 2-amino-2-(4-methylpheny)-acetyl | Isobutylthio | H | Butoxy | Butoxy |
| 2-amino-2-(benzo-thien-3-yl)acetyl | Formamido | H | Isopropoxy | Isopropoxy |
| 2-carboxy-2-(benzothien-2-yl)-acetyl | Methoxy | H | Sec-Butoxy | Sec-Butoxy |
| 2-oxo-2-phenylacetyl | Ethoxy | H | Tert-Butoxy | Tert-Butoxy |
| 2-oxo-2-(2-amino-thiazol-4-yl)acetyl | Propoxy | H | Pentyloxy | Pentyloxy |
| 2-(2-chloro-thiazol-4-yl)-2-methoxyimino-acetyl | Methylthio | H | Isopenthyloxy | Isopentyloxy |
| 2-(2-amino-thiazol-4-yl)-2-(2-carbamoyl-prop-2-yl)oxy-iminoacetyl | Ethylthio | H | Neopentyloxy | Neopentyloxy |
| acetyl | Isopropylthio | H | 3-Methylpentyloxy | 3-Methylpentyloxy |
| n-propionyl | n-Butylthio | H | 3-Methylbutoxy | 3-Methylbutoxy |
| t-butyryl | isobutylthio | H | 2-Ethylpropoxy | 2-Ethylpropoxy |
| n-valeryl | Formamido | H | 2,2-Dimethyl-butoxy | 2,2-Dimethyl-butoxy |

A preferred group of C-3 phosphine oxide substituted carbacephalosporins is represented by the Formula I wherein R is the substituted methyl group

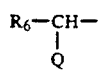

particularly those compounds wherein Q is amino and R$_6$ is phenyl, hydroxyphenyl, thienyl, or benzothienyl. Examples of such substituents, together with the CO moiety to which they are attached, are D-phenylglycyl, D-4-hydroxyphenylglycyl, D-2-thienylglycyl, D-benzothien-3-ylglycyl, and like functionalities.

A further preferred group is represented by Formula I wherein R is the group

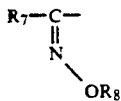

in the syn form.

Particularly preferred compounds are represented when $R_8$ is hydrogen, $C_1$-$C_4$ alkyl, a halo substituted $C_1$-$C_4$ alkyl group such as chloromethyl, bromoethyl, 3-chlorobutyl, and 4-fluorobutyl, or a carboxy substituted $C_1$-$C_4$ alkyl group such as carboxymethyl, 2-carboxyethyl, 3-carboxypropyl, and 2-carboxy-2-propyl; and $R_7$ is a five or six membered heterocyclic ring $R_5$ group, in particular, an amino substituted heterocyclic. Especially preferred heterocyclics are the 2-aminothiazole or 2-aminooxazole ring. Examples of such preferred RCO- groups are (2-aminothiazol-4-yl)-(methoxyimino)acetyl, (2-aminooxazol-4-yl)-(methoxyimino)acetyl, and the like.

A particularly preferred group is represented by Formula I wherein R is the group

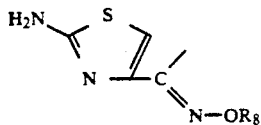

A further preferred group of C-3 phosphine oxide substituted carbacephalosporins is represented by the Formula I wherein $R_3$ and $R_4$ are —$OR_{11}$.

Particularly preferred compounds are represented when $R_{11}$ is $C_1$-$C_6$ alkyl.

A further preferred group of C-3 phosphine oxide substituted carbacephalosporins is represented by the Formula I wherein $R_2$ is hydrogen.

A further preferred group of C-3 phosphine oxide substituted carbacephalosporins is represented by the Formula I wherein $R_1$ is hydrogen, methoxy, methylthio or formamido.

Particularly preferred compounds are represented when $R_1$ is hydrogen.

The preferred compounds represented by Formula I are those which are formed by choosing substituents for A, $R_1$, $R_2$, $R_3$, and $R_4$ from the preferred groups represented above.

The compounds represented by Formula I can be prepared according to the route outlined in Scheme I. In Scheme I, A, R, $R_1$, $R_2$, $R_3$, and $R_4$ have the same meanings as defined above for Formula I.

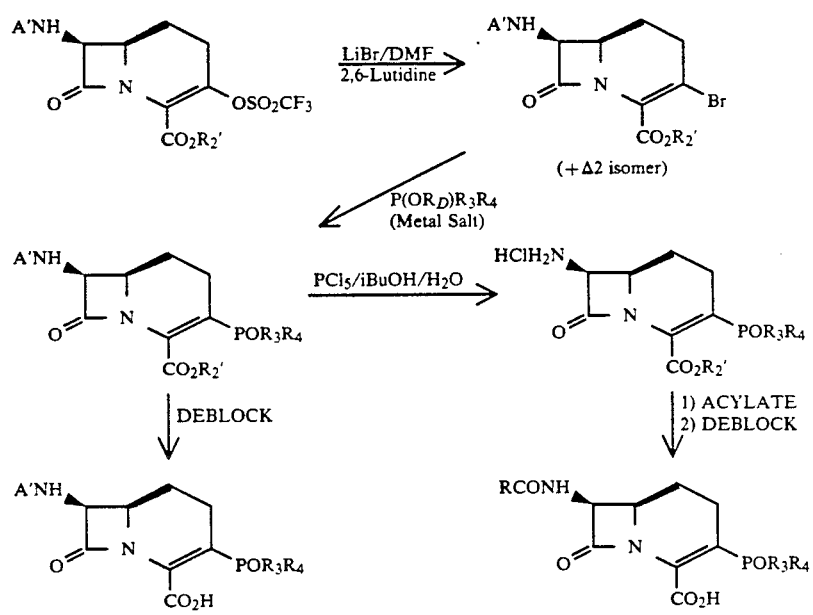

In this scheme A' is an amino-protecting group and $R_2$' is a carboxy-protecting group. The 3-trifluoromethanesulfonoxy (triflate or TF) carbacephem starting material may be prepared by the method of Evans et al., U.S. Pat. No. 4,673,737, or according to the method reported in *J. Med. Chem.*, 33, 1656-1662 (1990), both of which are incorporated herein by reference.

The 3-triflate may be converted to the 3-bromo intermediate by a displacement reaction using LiBr in the presence of a base such as 2,6-lytidine and an organic solvent. Suitable solvents include tetrahydrofuran, methylenechloride, dimethylformamide, and di- or trichloroethane. The displacement takes place at an elevated temperature (60°–70° C.) over an extended period of time, (16–48 hours). The reaction mixture is cooled to ambient temperature and a portion of the solvent is removed under reduced pressure at 50° C. The remaining slurry is diluted with ethyl acetate/ether, washed with NaHCO$_3$ (3×), 1N HCl (3×), and brine, dried over MgSO$_4$, filtered through silica gel with 10% ethyl acetate/CH$_2$Cl$_2$, and evaporated at reduced pressure until a solid begins to precipitate out. The solid is collected and further evaporation of the mother liquor may be carried out to obtain more solid. The solids from the mother liquors and the precipitate are combined and the remaining liquid is stripped to dryness. At this point there is a mixture of Δ-2/Δ-3 isomer. The mixture of the isomer may be equilibrated by dissolving the mixture in anhydrous CH$_2$Cl$_2$ followed by treatment with diazabicylcoundecene (DBU). After an extended time, (approximately three hours), at ambient temperature, the reaction is filtered through silica gel with 10% ethyl acetate/$CH_2Cl_2$ and thereafter evaporated. The residue is then dissolved in a small amount of ethyl acetate and diluted with hexane and cooled to 0° C.

The mixture may be further processed by dissolving it in ethyl acetate, diluting it in hexane, seeded with the product desired and thereafter chilling to 0° C. The 3-bromocarbaceph may then be used to prepare the 3-phosphine oxide substituted carbaceph.

The 3-bromo carbaceph is exposed to a trivalent phosphine oxide compound containing the group $-OR_D$, wherein $R_D$ is a leaving group and preferably is a $C_1$-$C_6$ alkyl. This process may be facilitated by the presence of a metal salt, such as Ni(II)$Cl_2$.

The 3-substituted carbacephalosporin may have the phenoxyacetyl group removed using known methodology, i.e., $PCl_5$/pyridine/isobutyl alcohol, to provide the hydrochloride as shown in Scheme I. The hydrochloride can then be acylated with di-t-butyldicarbonate (t-boc)$_2$O) followed by treatment with a base such as LiOH to provide the 7-$\beta$, t-butoxyamino intermediate (not shown). (Further details of this interchange of the t-butoxycarbonyl protecting group for the phenoxyacetyl protecting group to be found in European Patent Application No. 8836996.5, Publication No. 0301877.)

The t-butoxycarbonyl (t-boc) can then be removed using known methodology, i.e., trifluoro acetic acid (TFA) in the presence of anisole. The resulting 3-substituted intermediate can then be treated with an activated form of the desired 7-acyl group (RCO). The benhydryl ester and any remaining t-butoxycarbonyl protecting groups can then be removed by treatment with tri-fluoracetic acid. While the phenoxyacetyl and t-butoxycarbonyl (t-boc) groups were used as amino protecting groups, and the benzhydryl group as a carboxy protecting group, one of ordinary skill in $\beta$-lactam chemistry will appreciate that other groups will serve as functional equivalents. Alternatively, the 4-carboxy group may be de-protected, i.e., the benzylhydryl group removed, to form the desired carbacephem having a protected amino group at the 7-position.

When $R_3$ and $R_4$ equal $-OR_{11}$ the three phosphine oxide compounds may be made via the Michaelis-Arbuzov reaction as set out in Chem. Rev. 81, 415 (1981). When $R_3$ and $R_4$ both equal $-OR_{11}$ or both equal $-R_{11}$ these compounds may be prepared according to the method disclosed in Synthesis, 1048 (1985). When $R_3$ and $R_4$ are both equal to $-OR_{11}$ or wherein one is $-OR_{11}$ and the other is $R_{11}$ the compounds may be prepared according to the method disclosed in Tetrahedron 26, 5529 (1970) or J. Org. Chem. 43, 985 (1978). The four references cited are all incorporated herein by reference.

The following Examples are provided to further illustrate the invention. It is not intended that the invention be limited in scope by reason of any of the following Examples.

In the following Examples, the terms nuclear magnetic resonance spectra, mass spectra, infra-red spectra, ultraviolet spectra, elemental analysis and high performance liquid chromatography are abbreviated NMR, MS, IR, UV, Anal. and HPLC, respectively. In addition, the adsorption maxima listed for the IR spectra are only those of interest and not all of the maxima observed. In the Examples the following abbreviations have the indicated meanings: DMF=dimethylformamide; THF=tetrahydrofuran; DIPEA=diisopropyethylamine; and t-Boc=t-butyloxy carbonyl. Also, V stands for

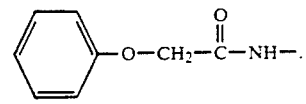

In conjunction with the NMR spectra, the following abbreviations are used: "s" is singlet, "d" is doublet, "dd" is doublet of doublets, "br. s" is broad singlet, "br. d" is a broad doublet, "t" is triplet, "q" is quartet, "m" is multiplet and "dm" is a doublet of multiplets. "J" indicates the coupling constant in Hertz. "DMSO/$d_6$" is dimethyl sulfoxide where all protons have been replaced with deuterium.

All reactions described herein were performed under an inert atmosphere of dry nitrogen in flame-dried glassware unless otherwise noted. All reagents were used as supplied unless stated otherwise. Melting points were recorded on a Thomas-Hoover apparatus and are uncorrected. $^1$H NMR spectra were recorded at 300 MHz with a General Electric QE-300 instrument. Chemical shifts are recorded in parts per million ($\delta$) relative to tetramethylsilane. IR spectra were recorded on a Nicolet MX-1 FT-IR, optical rotations were measured on a Perkin-Elmer 241 spectrometer, and UV spectra were obtained on a Cary 219. The mass spectra data were obtained on either a CEC-21-140 or a Varian MAT-731 spectrometer. All MPLC separations were conducted on Merck Lobar columns (LiChroprep RP-18) with the help of a Fluid Metering Inc. pump. Analytical HPLC separations were performed on a Varian chromatographic system utilizing a MicroPak MCH-5N-cap 15 cm $\times$ 4 mm column and a variable wavelength UV detector set to record at 254 nm.

EXAMPLE 1

7-[(Phenoxyacetyl)amino]-8-oxo-3-(diethoxyphosphinyl)-1-azabicyclo[4.2.0]oct-2-ene-2-carboxylic acid (diphenylmethyl)ester

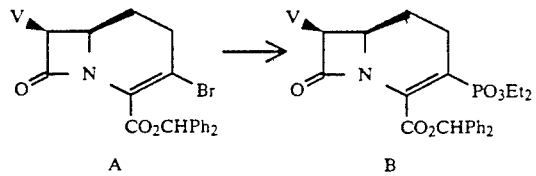

A solution of 3-bromo-7-[(phenoxyacetyl)amino]-8-oxo-1-azabicyclo[4.2.0]oct-2-ene-2-carboxylic acid (diphenylmethyl)ester (784 mg, 1.4 mmol) in triethyl phosphite (4 mL) was refluxed under nitrogen for 90 minutes. After cooling, the reaction was poured into hexanes. The supernatant liquid was decanted from the resulting semi-solid which was then dissolved in ethyl acetate and purified by flash-chromatography on silica gel (50% ethyl acetate/hexanes to 100% ethyl acetate) to provide 7-[(phenoxyacetyl)amino]-8-oxo-3-(diethoxyphosphinyl)-1-azabicyclo[4.2.0]oct-2-ene-2-carboxylic acid (diphenylmethyl) ester (100 mg; 16%):

m.p. 70°-74° C.

$^1$H NMR (CDCl$_3$, 300 MHz) $\delta$7.50–7.22 (m, 13H), 7.08–6.88 (m, 4H), 5.46–5.38 (m, 1H), 4.54 (s, 2H), 4.04–3.80 (m, 5H), 2.62–2.26 (m, 1H), 2.40–2.24 (m, 1H), 1.98–2.06 (m, 1H), 1.46–1.28 (m, 1H), 1.17 (dt, J=24, 6 Hz, 6H).

IR (CHCl₃) 3420, 3000, 1783, 1245, 1243, 1225, 1220, 1217, 1046, 1023 cm⁻¹.
MS (FAB) 619 (M+).
UV (EtOH) 269 nm (E=13200).
[a]²⁵365° −277.9° (c=0.00637,DMSO).

EXAMPLE 2

7-[(phenoxyacetyl)amino]-8-oxo-3-(diethoxyphosphinyl)-1-azabicyclo[4.2.0]oct-2-ene-2-carboxylic acid sodium salt

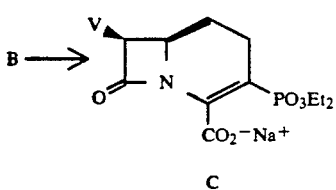

C

To a solution of 7-[(phenoxyacetyl)amino]-8-oxo-3-(diethoxyphosphinyl)-1-azabicyclo[4.2.0]oct-2-ene-2-carboxylic acid (diphenylmethyl) ester (450 mg, 0.73 mmol) in methanol (50 mL) was added 5% palladium on carbon (100 mg). The mixture was stirred under an atmosphere of hydrogen at room temperature overnight. The reaction was filtered and the solvent removed. The residue was treated with aqueous sodium bicarbonate and the soluble material chromatographed by medium pressure liquid chromatography on a C₁₈ column eluted with 100% water to 20% acetonitrile/water. The product-containing fractions were lyophilized to give 17 mg (4.9%) of the titled product.

m.p.>200° C. (d).

¹H NMR (DMSO-d₆, 300 MHz) δ9.20–8.93 (m, 1H), 7.29–7.24 (m, 2H), 6.95–6.89 (m, 3H), 5.56–5.24 (m, 1H), 4.54 (s, 2H), 4.15–3.86 (m, 4H), 3.79–3.65 (m, 1H), 2.25–1.92 (m, 2H), 1.70–1.52 (m, 2H), 1.24–1.11 (m, 6H).

MS (FAB) 475 (M+1), 497 (M+23).

EXAMPLE 3

7-[(Phenoxyacetyl)amino]-8-oxo-3-(dimethoxyphosphinyl)-1-azabicyclo[4.2.0]oct-2-ene-2-carboxylic acid (diphenylmethyl)ester

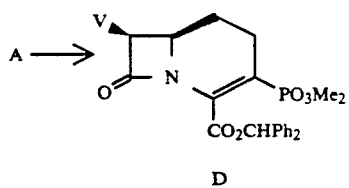

D

A solution of 3-bromo-7-[(phenoxyacetyl)amino]-8-oxo-1-azabicyclo[4.2.0]oct-2-ene-2-carboxylic acid (diphenylmethyl)ester (1.12 g, 2 mmol) in trimethyl phosphite (5 mL) was refluxed under nitrogen for two hours. After cooling, the reaction was poured into hexanes. The supernatant was removed and the residue purified by flash chromatography on silica gel (50% ethyl acetate/hexanes to 100% ethyl acetate) to provide 7-[(phenoxyacetyl)amino]-8-oxo-3-(dimethoxyphosphinyl)-1-azabicyclo[4.2.0]oct-2-ene-2-carboxylic acid (diphenylmethyl)ester (300 mg; 25%):

¹H NMR (CDCl₃, 300 MHz) δ7.53–7.25 (m, 13H), 7.18–6.90 (m, 4H), 5.49–5.45 (m, 1H), 4.55 (s, 2H), 4.00–3.93 (m, 1H), 3.53 (d, J=12 Hz, 3H), 3.45 (d, J=12 Hz, 3H), 2.65–2.48 (m, 1H), 2.42–2.25 (m, 1H), 2.10–1.95 (m, 1H), 1.56–1.35 (m, 1H).

MS (FAB) 591 (M+1).

EXAMPLE 4

7-[(phenoxyacetyl)amino]-8-oxo-3-(dimethoxyphosphinyl)-1-azabicyclo[4.2.0]oct-2-ene-2-carboxylic acid sodium salt

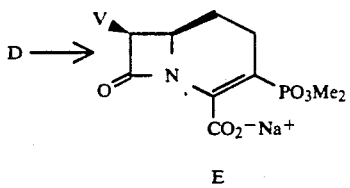

E

To a solution of 7-[(phenoxyacetyl)amino]-8-oxo-3-(dimethoxyphosphinyl)-1-azabicyclo[4.2.0]oct-2-ene-2-carboxylic acid (diphenylmethyl)ester (300 mg, 0.51 mmol) in methanol (50 mL) was added 5% palladium on carbon (100 mg). The mixture was stirred at room temperature under an atmosphere of hydrogen for two hours. The reaction was filtered and the solvent removed. The residue was treated with aqueous sodium bicarbonate and the soluble material chromatographed by medium pressure liquid chromatography on a C₁₈ column eluted with 100% water to 90% acetonitrile/water. The product-containing fractions were lyophilized to give 94 mg (42%) of the titled product.

m.p.>200° C. (d);

1H NMR (DMSO-d₆, 300 MHz) δ9.03 (d, J=9 Hz, 1H), 7.29–7.24 (m, 2H), 6.95–6.89 (m, 3H), 5.32–5.27 (m, 1H), 4.55 (s, 2H), 3.72–3.68 (m, 1H), 3.58–3.53 (m, 6H), 2.22–1.96 (m, 2H), 1.70–1.56 (m, 2H).

IR (KBr) 3420, 1764, 1684, 1599, 1540, 1494, 1243, 1059, 1026 cm⁻¹.

MS (FAB) 447 (M+1), 469 (M+23).

UV (EtOH) 268 nm (E=12,900).

[a]²⁵365° +89.66° (c=0.000435, DMSO).

EXAMPLE 5

7-[(Phenoxyacetyl)amino]-8-oxo-3-(dibutoxyphosphinyl)-1-azabicyclo[4.2.0]oct-2-ene-2-carboxylic acid sodium salt

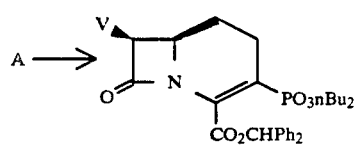

F

A solution of 3-bromo-7-[(phenoxyacetyl)amino]-8-oxo-1-azabicyclo[4.2.0]oct-2-ene-2-carboxylic acid (diphenylmethyl)ester (2 g, 3.6 mmol) in toluene (50 mL) was added tri-n-butyl phosphite (15 mL) and nickel(II)-chloride (50 mg, 039 mmol). The reaction was brought to reflux under nitrogen. Each hour, the reaction was cooled and an additional portion of nickel(II)chloride (50 mg, 0.39 mmol) was added. This process was continued for a total of six hours. The reaction was concentrated in vacuo and the residue purified by flash chromatography on silica gel (25%–50% ethyl acetate/hexanes) to provide 7-[(Phenoxyacetyl)amino]-8-oxo-3-

(dibutoxyphosphinyl)-1-azabicyclo[4.2.0]-oct-2-ene-2-carboxylic acid (diphenylmethyl)ester (588 mg, 24%):

¹H NMR (CDCl₃, 300 MHz) δ7.50–7.25 (m, 13H), 7.15–6.90 (m, 4H), 5.45–5.40 (m, 1H), 4.55 (s, 2H), 4.19–3.70 (m, 5H), 2.62–2.48 (m, 1H), 2.40–2.25 (m, 1H), 2.10–1.95 (m, 1H), 1.75–1.20 (m, 9H), 1.00–0.82 (m, 6H).

MS (FAB) 675 (M+1).

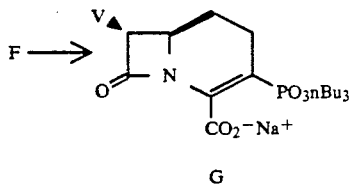

B.

G

To a solution of 7-[(phenoxyacetyl)amino]-8-oxo-3-(dibutoxyphosphinyl)-1-azabicyclo[4.2.0]-oct-2-ene-2-carboxylic acid (diphenylmethyl)ester (575 mg, 0.85 mmol) in methanol (20 mL) was added 5% palladium on carbon (previously wetted with absolute ethanol). The mixture was stirred at room temperature under an atmosphere of hydrogen overnight. The following day, the reaction was filtered and the solution treated with a fresh portion of catalyst (70 mg). The mixture was stirred at room temperature under an atmosphere of hydrogen for six hours. The mixture was filtered and the filtrate concentrated in vacuo. The residue was stirred with a mixture of chloroform and saturated aqueous sodium bicarbonate. The aqueous portion was separated and chromatographed by medium pressure liquid chromatography on a C₁₈ column eluted with 100% water to 80% acetonitrile/water. The product-containing fractions were lyophilized to give 55 mg (12%) of 7-[(phenoxyacetyl)amino]-8-oxo-3-(dibutoxyphosphinyl)-1-azabicyclo[4.2.0]-oct-2-ene-2-carboxylic acid sodium salt:

m.p.>120° C.

¹H NMR (DMSO-d₆, 300 MHz) δ9.10–8.96 (m, 1H), 7.29–7.24 (m, 2H), 6.95–6.89 (m, 3H), 5.33–5.25 (m, 1H), 4.54 (s, 2H), 3.96–3.82 (m, 4H), 3.76–3.65 (m, 1H), 2.22–1.96 (m, 2H), 1.70–1.48 (m, 6H), 1.40–1.25 (m, 4H), 0.88–0.81 (m, 6H).

IR (KBr) 3420, 2960, 1773, 1680, 1620, 1485, 1395, 1246, 1220, 1066, 1024 cm⁻¹.

MS (FAB) 531 (M+1), 553 (M+23).

UV (EtOH) 268 nm (E=14,300).

[a]²⁵365° −6.00° (c=0.005, DMSO).

EXAMPLE 6

7-[(Phenoxyacetyl)amino]-8-oxo-3-phosphinyl-1-azabicyclo[4.2.0]oct-2-ene-2-carboxylic acid

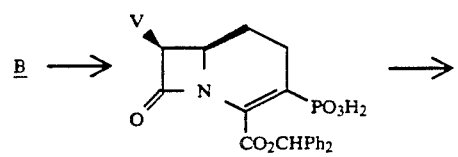

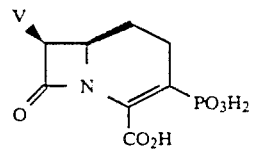

H

A solution of 7-[(phenoxyacetyl)amino]-8-oxo-3-(diethoxyphosphinyl)-1-azabicyclo[4.2.0]oct-2-ene-2-carboxylic acid (diphenylmethyl)ester (618 mg, 1 mmol) in methylene chloride (20 mL) was cooled to 0° C. under nitrogen. Bromotrimethylsilane (612 mg, 4 mmol) was added and the stirred reaction warmed to room temperature. After two hours, the solvent was removed in vacuo. The residue was stirred at room temperature with methanol-water for 0.5 hours. The reaction product was concentrated and (1 mmol) of the product was treated with trifluoroacetic acid (10 mL) and triethylsilane (4 mL) and stirred vigorously for one hour. The volatiles were removed in vacuo and the residue purified by flash chromatography on silica gel (21/7/7/9 ethyl acetate/acetonitrile/acetic/acid/water) followed by medium pressure liquid chromatography on a C₁₈ column eluted with 10% to 20% acetonitrile/water. The fractions containing pure product were combined and lyophilized to yield 20 mg (5%) 7-[(phenoxyacetyl)amino]-8-oxo-3-phosphinyl-1-azabicyclo[4.2.0]-oct-2-ene-2-carboxylic acid:

m.p.>180 (d).

¹H NMR (DMSO-d₆, 300 MHz) δ8.83 (d, J=9 Hz, 1H), 7.30–7.24 (m, 2H), 6.95–6.90 (m, 3H), 5.29–5.25 (m, 1H), 4.55 (s, 2H), 3.80–3.60 (m, 1H), 2.74–2.59 (m, 1H), 2.30–2.12 (m, 1H), 1.74–1.47 (m, 2H).

IR (KBr) 3325, 3070, 2940, 1765, 1683, 1599, 1538, 1493, 1380, 1237, 1064, 1022 cm⁻¹.

MS (FAB) 397(M+), 419(M+23); UV (EtOH) 269 nm (E=11,300).

[a]²⁵365° +102.22° (c=0.00225, DMSO).

The compounds of Formula I inhibit the growth of certain pathogenic organisms as demonstrated by agar dilution method in which test compounds were diluted to an appropriate range of concentrations in 0.1M phosphate buffer, pH 7.0, incorporated into Mueller-Hinton agar (Difco) supplemented with 1% Bacto-Supplement C (Difco) at 50° C. and allowed to solidify in petri dishes. Fresh overnight cultures of test bacteria were diluted to approximately 1×(10)4 cells/microliter and applied in one microliter volumes to the surfaces of the agar plates. The innoculated plates were incubated overnight at 35° C. in ambient air. Minimum inhibitory concentration (mic) endpoints were recorded as the lowest antibiotic concentrations in micrograms per milliliter that inhibited the development of visible growth on the plates. Table 2 summarizes the results of such test with the compounds of the examples listed above.

TABLE 2

| COMPOUND | S.aureus (X1.1) | S.epi (222) | S.pneumonia (PARK) | E.coli (EC14) |
|---|---|---|---|---|
| 7-[(phenoxyacetyl)amino]-8-oxo-3-(diethoxyphosphinyl)-1-azabicyclo[4.2.0]oct-2-ene-2-carboxylic acid sodium salt | 0.25 | 1.0 | 0.25 | 64 |

TABLE 2-continued

| COMPOUND | S.aureus (X1.1) | S.epi (222) | S.pneumonia (PARK) | E.coli (EC14) |
|---|---|---|---|---|
| 7-[(phenoxyacetyl)amino]-8-oxo-3-(dimethoxyphosphin-yl)-1-azabicyclo[4.2.0]oct-2-ene-2-carboxylic acid sodium salt | 0.5 | 1.0 | 0.5 | 64 |
| 7-[(phenoxyacetyl)amino]-8-oxo-3-(dibutoxyphosphin-yl)-1-azabicyclo[4.2.0]oct-2-ene-2-carboxylic acid sodium salt | 0.5 | 1.0 | 0.03 | >128 |
| 7-[(phenoxyacetyl)amino]-8-oxo-3-phosphinyl-1-azabicyclo[4.2.0]oct-2-ene-2-carboxylic acid | 64 | >128 | >128 | >128 |

The antimicrobial compounds of this invention are useful for the therapeutic or prophylactic treatment of infections in warm-blooded animals caused by both gram-positive, gram-negative and acid-fast bacteria.

The antimicrobial can be administered orally, parenterally (e.g. intravenously, intramuscularly or subcutaneously) or as a topical ointment or solution in treating bacterial infections of warm-blooded animals.

A further aspect of this invention is the pharmaceutical compositions of the antimicrobial compounds of Formula I. In particular, these pharmaceutical compositions are useful for the control of gram-positive and gram-negative bacterial infections and comprise a suitable vehicle and a therapeutically effective amount of the antimicrobial compounds of Formula I.

With regard to compositions for oral administration (e.g. tablets and capsules), the term "suitable vehicle" means common excipients such as binding agents, for example, syrup, acacia, gelatin, sorbitol, tragacanth, polyvinylpyrrolidine (Povidone), methylcellulose, ethylcellulose, sodium carboxymethylcellulose, hydroxypropylmethylcellulose, sucrose and starch; fillers and carriers, for example corn starch, gelatin, lactose, sucrose, microcrystalline cellulose, kaolin, mannitol, dicalcium phosphate, sodium chloride and alginic acid; disintegrators such as microcrystalline cellulose, corn starch, sodium starch glycolate, alginic acid; and lubricants such as magnesium stearate and other metallic stearates, stearic acid, silicone fluid, talc, waxes, oils and colloidal silica. Flavoring agents such as peppermint, oil of wintergreen, cherry flavoring or the like can also be used. It may be desirable to add a coloring agent to make the dosage form more aesthetically pleasing in appearance or to help identify the product. The tablets may also be coated by methods well known in the art.

The pharmaceutical compositions of the present invention may also be in the form of oral liquid preparations, which may be either a) aqueous or oily suspensions, solutions, emulsions or syrups; or b) a dry powder to be reconstituted with water or another suitable vehicle before use. When used in conjunction with such oral liquid preparations, the term "suitable vehicle" means conventional additives such as suspending agents, for example, sorbitol, syrup, methyl cellulose, glucose/sugar syrup, gelatin, hydroxyethylcellulose, carboxymethylcellulose, aluminum stearate gel or hydrogenated edible oils, for example almond oil, fractionated coconut oil, oily esters, propylene glycol or ethyl alcohol; and preservatives such as methyl or propyl p-hydroxybenzoates or sorbic acid.

The pharmaceutical composition can also be for intravenous (IV) use. Specifically, a water soluble form of the antimicrobial compound can be dissolved in one of the commonly used intravenous fluids and administered by infusion. When used in conjunction with compositions for IV use, the term "suitable vehicle" means such fluids as physiological saline, Ringer's solution or 5% dextrose solution.

For intramuscular preparations a sterile formulation of a suitable salt form of the antimicrobial compound (for example, the hydrochloric salt or sodium salt) can be formulated with a "suitable vehicle". Examples of scuh sterile formulations are a suitable salt form either dissolved in a pharmaceutical diluent (for example, Water-for-Injection, physiological saline, 5% glucose) or suspended in an aqueous base or a pharmaceutically acceptable oil base (for example, an ester of a long chain fatty acid such as ethyl oleate).

Topical compositions can be formulated with "suitable vehicles" such as hydrophobic or hydrophilic bases. Such bases include ointments, creams or lotions.

Veterinary pharmaceutical compositions of the antibiotic compounds may be administered in the feed or the drinking water of farm animals. Alternatively, the compounds can be formulated as intramammary preparations with "suitable vehicles" such as long- or quick-release bases.

The antimicrobial compounds of Formula I can be used as surface disinfecants. Solutions containing as little as 0.1 percent by weight of the antimicrobial compound are effective for disinfecting purposes. Preferably, such solutions also can contain a detergent or other cleansing agent. The solutions are useful for disinfecting objects such as glassware, dental and surgical instruments, and surfaces such as walls, floors, and tables in areas where maintenance of sterile conditions is important, for example, hospitals, food-preparation areas, and the like.

The antimicrobial compounds of Formula I can also be formulated in unit dosage form in sterile vials, sterile plastic pouches containing a port with a septum, or sterile, hermetically sealed ampoules. The antimicrobial compound (or the corresponding pharmaceutically-acceptable salt) may be a dry powder or in crystalline or lyophilized form. The amount of the anti-microbial compound per unit dosage may vary from about 250 milligrams to about 10 grams.

A "therapeutically effective amount" of the antimicrobial compounds of Formula I is from approximately 3.5 mg to about 50 mg of compound per kilogram of body weight. This amount generally totals from about 1 gram to about 27 grams per day for an adult human.

A further aspect of this invention is a method for treating or controlling infectious diseases caused by gram-positive and gram-negative organisms in warm-blooded animals. This method comprises administering to the animal a therapeutically effective amount of the instant antimicrobial compounds. A typical daily dose for an adult human in this method is from about 1 gram to about 12 grams.

In practicing this method, the antibiotic can be administered in a single daily dose or in multiple doses per day. The treatment regime may require administration over extended periods of time, e.g., for several days or for from two to three weeks. The amount administered per dose or the total amount administered will depend on such factors as the nature and severity of the infection, the age and general health of the patient, the tolerance of both the patient and the microorganism or microorganisms involved in the infection to the antimicrobial compound.

The following formulation examples represent specific pharmaceutical formulations employing compounds comprehended by the present method. The formulations may employ as active compounds any of the compounds of Formula I or a pharmaceutically acceptable salt or biologically labile ester thereof. The examples are illustrative only and are not intended to limit the scope of the invention in any way.

FORMULATION 1

Hard gelatin capsules are prepared using the following ingredients:

|  | Quantity (mg/capsule) |
| --- | --- |
| Example | 1250 |
| Starch dried | 200 |
| Magnesium stearate | 10 |

The above ingredients are mixed and filled into hard gelatin capsules in 460 mg quantities.

FORMULATION 2

A tablet formula is prepared using the ingredients below:

|  | Quantity (mg/tablet) |
| --- | --- |
| Example 2 | 250 |
| Cellulose, microcrystalline | 400 |
| Silicon dioxide, fumed | 10 |
| Stearic acid | 5 |
| Magnesium stearate | 10 |

The components are blended and compressed to form tablets each weighing 675 mg.

FORMULATION 3

An aerosol solution is prepared containing the following components:

|  | Weight |
| --- | --- |
| Example 3 | 0.25 |
| Ethanol | 29.75 |
| Propellant 22 (Chlorodifluoromethane) | 70.00 |

The active compound is mixed with ethanol and the mixture added to a portion of the propellant 22, cooled to −30° C. and transferred to a filling device. The required amount is then placed in a stainless steel container and diluted with the remainder of the propellant. The valve units are then fitted to the container.

FORMULATION 4

Tablets each containing 60 mg of active ingredient are made up as follows:

| Example 4 | 60 mg |
| --- | --- |
| Starch | 45 mg |
| Microcrystalline cellulose | 35 mg |
| Polyvinylpyrrolidone (as 10% solution in water) | 4 mg |
| Sodium carboxymethyl starch | 4.5 mg |
| Magnesium stearate | 0.5 mg |
| Talc | 1 mg |

The active ingredient, starch and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 40°–60° C. and passed through a No. 18 mesh U.S. sieve. The sodium carboxymethyl starch, magnesium stearate and talc, previously passed through a No. 60 mesh U.S. sieve, are then added to the granules which, after mixing, are compressed on a tablet machine to yield tablets each weighing 150 mg.

FORMULATION 5

Capsules each containing 80 mg of medicament are made as follows:

| Example 1 | 80 mg |
| --- | --- |
| Starch | 59 mg |
| Microcrystalline cellulose | 59 mg |
| Silicone fluid | 2 mg |

The active ingredient, cellulose, starch and magnesium stearate are blended, passed through a No. 45 mesh U.S. sieve, and filled into hard gelatin capsules in 200 mg quantities.

FORMULATION 6

Suppositories each containing 225 mg of medicament are made as follows:

| Example 2 | 225 mg |
| --- | --- |
| Saturated fatty acid glycerides to | 2 mg |

The active ingredient is passed through a No. 60 mesh U.S. sieve and suspended in the saturated fatty acid glycerides previously melted using the minimum heat necessary. The mixture is then poured into a suppository mold of nominal 2 g capacity and allowed to cool.

FORMULATION 7

As intravenous formulation is prepared as follows:

| Example 3 | 100 mg |
| --- | --- |
| Isotonic saline | 1000 ml |

The solution of the above ingredients is administered intravenously at a rate of 1 ml/minute to a mammal in need of treatment.

I claim:

1. A compound of the Formula (I)

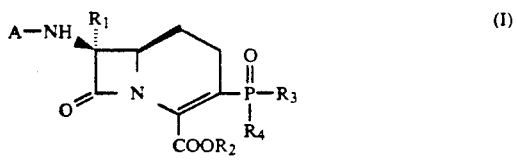

wherein $R_1$ is hydrogen, $C_1$-$C_4$ alkoxy, $C_1$-$C_4$ alkylthio, or the formido group —NHCHO; $R_2$ is hydrogen, a biologically labile group, or a carboxy-protecting group; $R_3$ and $R_4$ independently are —$OR_{11}$ or —$R_{11}$ wherein $R_{11}$ is $C_1$-$C_6$ alkyl, $C_2$-$C_6$ alkenyl, $C_2$-$C_6$ alkynyl, $C_1$-$C_6$ substituted alkyl, $C_2$-$C_6$ substituted alkenyl, $C_2$-$C_6$ substituted alkynyl, phenyl, or a substituted phenyl group represented by the formula

wherein a and a' independently are hydrogen, halogen, hydroxy, $C_1$-$C_4$ alkoxy, $C_1$-$C_4$ alkanoyloxy, $C_1$-$C_4$ alkyl, $C_1$-$C_4$ alkylthio, amino, $C_1$-$C_4$ alkanoylamino, $C_1$-$C_4$ alkyl-sulfonylamino, carboxy, carbamoyl, hydroxymethyl, amino-methyl, or carboxymethyl; and A is hydrogen or an amino-protecting group; and the pharmaceutically acceptable salts thereof.

2. The compound as recited in claim 1 wherein A is of the formula

wherein R is $C_1$-$C_6$ alkyl, $C_1$-$C_6$ alkyl substituted by cyano, carboxy, halogen, amino, $C_1$-$C_4$ alkoxy, $C_1$-$C_4$ alkylthio, trifluoromethyl, trifluoromethylthio; naphthyl, a phenyl or a substituted phenyl group represented by the formula

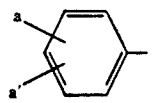

wherein a and a' are as defined previously; a group represented by the formula

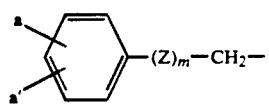

wherein a and a' are defined as above, Z is O or S, and m is 0 or 1;

a heteroarylmethyl group represented by the formula $R_5$—CH$_2$— wherein $R_5$ is thienyl, furyl, benzothienyl, benzofuryl, indolyl, triazolyl, tetrazolyl, oxazolyl, thiazolyl, oxadiazolyl, thiadiazolyl, and such heteroaryl groups substituted by amino, hydroxy, halogen, $C_1$-$C_4$ alkyl, $C_1$-$C_4$ alkoxy, or $C_1$-$C_4$ alkylsulfonylamino;

a substituted methyl group represented by the formula $$R_6\text{—CH—}Q$$

wherein $R_6$ is cyclohex-1,4-dienyl, or an optionally substituted phenyl group represented by the formula

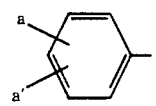

wherein a and a' have the above defined meanings, or $R_6$ is $R_5$ as defined above, and Q is amino, hydroxy, $C_1$-$C_4$ alkanoyloxy, carboxy, sulfoamino, or a substituted amino group of the formula

wherein $R^x$ is hydrogen or $C_1$-$C_3$ alkyl, $R^y$ is $C_1$-$C_4$ alkyl, furyl, thienyl, phenyl, halophenyl, nitrophenyl, styryl, halostyryl, nitrostyryl or a group of the formula

wherein $R^x$ has the same meanings as defined above and $R^z$ is hydrogen, $C_1$-$C_3$ alkylsulfonyl, $C_1$-$C_3$ alkyl, or $C_1$-$C_4$ alkanoyl; or Q is a substituted amino group of the formula

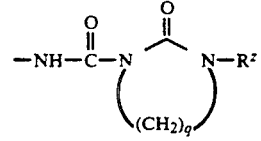

wherein $R^z$ has the same meanings as defined above, and q is 2 or 3; or Q is a substituted amino group of the formula

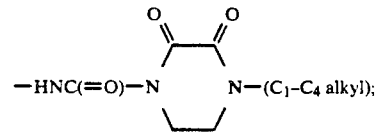

or Q is a benzamido group of the formula

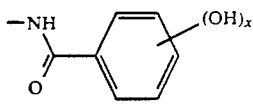

wherein x is 1 to 3;
or Q is a pyridonylcarbonylamino group of the formula

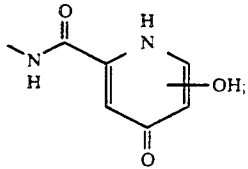

or Q is a pyridylcarbonylamino group of the formula

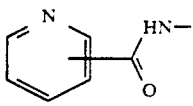

said group optionally substituted by $C_1$-$C_4$ alkyl, amino, carboxy, hydroxy or halogen; or Q is an imidazolyl or pyrazolyl group of the formula

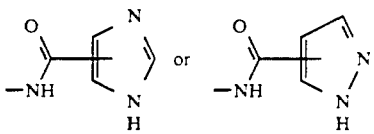

and said imidazolyl or pyrazolyl optionally substituted by $C_1$-$C_4$ alkyl, carboxy, amino, or halogen; or Q is a benzpyridazin-4-one group represented by the formula

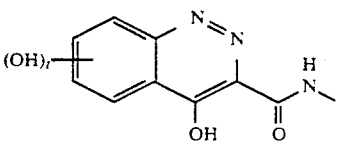

or

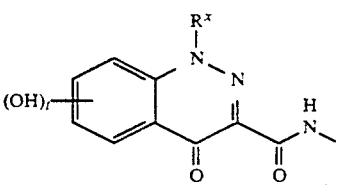

wherein $R^x$ is hydrogen or $C_1$-$C_3$ alkyl, and t is 1 to 3; or Q is a benzpyranone group of the formula

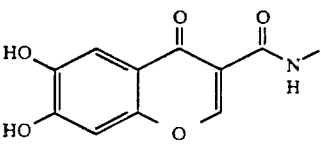

or R is a group represented by the formula

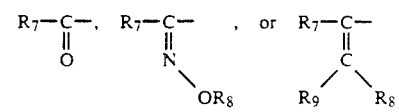

wherein $R_7$ is $R_5$ or $R_6$ as defined above, $R_9$ is hydrogen or halogen, and $R_8$ is hydrogen, $C_1$-$C_4$ alkyl, or a group represented by the formula

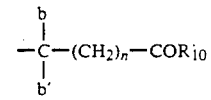

wherein b and b' independently are hydrogen or $C_1$-$C_3$ alkyl, or b and b', when taken together with the carbon to which they are bonded, form a 3- to 6-membered carbocyclic ring, n is 0-3, and $R_{10}$ is hydroxy, $C_1$-$C_4$ alkoxy, amino, $C_1$-$C_4$ alkylamino, or di($C_1$-$C_4$ alkyl)-amino; or $R_8$ is $C_1$-$C_4$ alkyl substituted by phenyl or phenyl substituted by one or two of the same or different groups selected from among $C_1$-$C_4$ alkyl, hydroxy, halogen, carboxy or protected carboxy; or $R_8$ is $C_1$-$C_4$ alkyl substituted by amino or protected amino; or $R_8$ is $C_2$-$C_4$ alkenyl; or $R_8$ is a cyclic lactam group of the formula

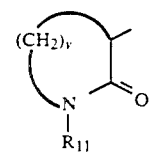

wherein v is 2-4 and $R_{11}$ is hydrogen or $C_1$-$C_3$ alkyl; or $R_8$ is a heteroaryl methyl group of the formula

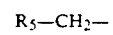

wherein $R_5$ has the same meanings as defined hereinabove.

3. The compound as recited in claim 2 wherein R is a substituted methyl group

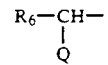

wherein Q is amino and $R_6$ is phenyl, hydroxyphenyl, thienyl, or benzothienyl.

4. The compound as recited in claim 2 wherein R is a group of the formula

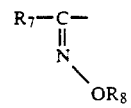

in the syn form.

5. The compound as recited in claim 4 wherein $R_8$ is hydrogen, $C_1$-$C_4$ alkyl, a halo substituted $C_1$-$C_4$ alkyl group or a carboxy substituted $C_1$-$C_4$ alkyl group and $R_7$ is $R_5$ as defined.

6. The compound as recited in claim 5 wherein $R_7$ is 2-aminothiazole or 2-aminooxizole.

7. The compound as recited in claim 2 wherein R is of the formula

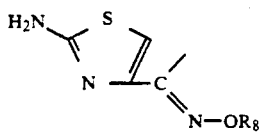

8. The compound as recited in claim 1 wherein $R_3$ and $R_4$ are $-OR_{11}$.

9. The compound as recited in claim 1 wherein $R_{11}$ is $C_1-C_6$ alkyl.

10. The compound as recited in claim 1 wherein $R_2$ is hydrogen.

11. The compound as recited in claim 1 wherein $R_1$ is hydrogen, methoxy, methylthio, or formamido.

12. A pharmaceutical formulation comprising a compound of claim 1 and a pharmaceutically-acceptable carrier, diluent or excipient therefore.

13. A pharmaceutical formulation comprising a compound of claim 2 and a pharmaceutically-acceptable carrier, diluent or excepient therefore.

14. A method of controlling infectious diseases caused by gram positive and gram negative organisms in warm blooded animals which comprises administering a therapeutically effective amount of a compound of claim 1.